US00PP22193P2

(12) United States Plant Patent
Hanes

(10) Patent No.: US PP22,193 P2
(45) Date of Patent: Oct. 11, 2011

(54) ***PETUNIA* PLANT NAMED 'PIC AMTHE'**

(50) Latin Name: *Petunia hybrida*
Varietal Denomination: Pic Amthe

(75) Inventor: Mitchell Hanes, Morgan Hill, CA (US)

(73) Assignee: Syngenta Crop Protection AG, Basel (CH)

( * ) Notice: Subject to any disclaimer, the term of this patent is extended or adjusted under 35 U.S.C. 154(b) by 132 days.

(21) Appl. No.: 12/657,237

(22) Filed: Jan. 15, 2010

(51) Int. Cl.
*A01H 5/00* (2006.01)

(52) U.S. Cl. ..... Plt./356.18

(58) Field of Classification Search ..... Plt./356.18
See application file for complete search history.

(56) References Cited

U.S. PATENT DOCUMENTS

| | | | | |
|---|---|---|---|---|
| PP13,553 | P2 * | 2/2003 | Dummen | Plt./356.18 |
| PP13,984 | P3 * | 7/2003 | Bessho | Plt./356.18 |
| PP16,439 | P2 * | 4/2006 | Brown | Plt./356.21 |
| PP17,291 | P2 * | 12/2006 | Oud | Plt./356.18 |

OTHER PUBLICATIONS

UPOV ROM GTITM Computer Database, GTI Jouve Retrieval Software 2011/01 Citation for 'Pic Amthe'.*
Anonymous. "Picnic Petunia hybrida" available at: http://www.syngentaflowersinc.com/pdf/cultural/PicnicPetunia.pdf accessed Jul. 16, 2011.*

* cited by examiner

*Primary Examiner* — Wendy C Haas
(74) *Attorney, Agent, or Firm* — S. Matthew Edwards

(57) ABSTRACT

A new *Petunia* plant named 'Pic Amthe' particularly distinguished by the small purple to purple-violet colored flowers, good floriferousness, slightly yellow-green foliage, initially semi-compact and then an outwardly spreading and somewhat upright plant habit, good vigor, well branched, with early and continuous flowering response.

1 Drawing Sheet

Latin name of the genus and species of the plant claimed: *Petunia hybrida.*

Varietal denomination: 'Pic Amthe'.

BACKGROUND OF THE NEW PLANT

The present invention comprises a new *Petunia*, botanically known as *Petunia hybrida*, and hereinafter referred to by the variety name 'Pic Amthe.'

'Pic Amthe' is a product of a planned breeding program. The new cultivar has small purple to purple-violet colored flowers, good floriferousness, slightly yellow-green foliage, initially semi-compact and then an outwardly spreading and somewhat upright plant habit, good vigor, well branched, with early and continuous flowering response.

'Pic Amthe' originated from a hybridization made in August 2004 in a controlled breeding environment in Gilroy, Calif. The seed was sown in February 2005. The female parent was the proprietary plant designated '1691-1,' unpatented, with blue-pink flower color, less vigor and a more open plant habit.

The male parent of 'Pic Amthe' is the commercially available variety identified as 'MP 209,' (U.S. Plant Pat. No. 16,439) with a rose colored flower. 'MP 209' is earlier to flower, has longer branches, and shorter peduncles than 'Pic Amthe.'

'Pic Amthe' was selected as one flowering plant within the progeny of the stated cross in May 2005 in a controlled environment in Gilroy, Calif.

The first act of asexual reproduction of 'Pic Amthe' was accomplished when vegetative cuttings were propagated from the initial selection in May 2005 in a controlled environment in Gilroy, Calif.

BRIEF SUMMARY OF INVENTION

Horticultural examination of plants grown from cuttings of the plant initiated in May 2005, and continuing thereafter, has demonstrated that the combination of characteristics as herein disclosed for 'Pic Amthe' are firmly fixed and are retained through successive generations of asexual reproduction.

'Pic Amthe' has not been observed under all possible environmental conditions. The phenotype may vary significantly with variations in environment such as temperature, light intensity and day length.

A Plant Breeder's Right for this cultivar was applied for in Canada on Jan. 30, 2009. 'Pic Amthe' has not been made publicly available more than one year prior to the filing of this application.

The following traits have been repeatedly observed and are determined to be basic characteristics of the new variety. The combination of these characteristics distinguishes this *Petunia* as a new and distinct variety.

BRIEF DESCRIPTION OF THE PHOTOGRAPHS

The accompanying photographic drawing shows typical flower and foliage characteristics of 'Pic Amthe' with colors being as true as possible with an illustration of this type. The photographic drawing shows a flowering potted plant of the new variety, and a close-up of the flowers, growing in a greenhouse in the winter in Gilroy, Calif.

DETAILED BOTANICAL DESCRIPTION

The plant descriptions, measurements and aforementioned photographs were taken in Gilroy, Calif. in January 2010 under natural light. These plants used in the photograph and descriptions were about 7-9 weeks old, directly grow from tissue culture stock.

Color references are made to The Royal Horticultural Society Colour Chart (R.H.S.) 2001.

TABLE 1

DIFFERENCES BETWEEN THE NEW VARIETY 'PIC AMTHE' AND A SIMILAR VARIETY

| | 'Pic Amthe' | 'MP 209' |
|---|---|---|
| Flower color: | Purple-violet | Rose |
| Flowering response: | Little later | Littler earlier |
| Branch length: | Shorter | Longer |
| Peduncle length: | Longer | Shorter |

Plant:

*Form, growth and habit.*—Initially semi-compact and then an outwardly spreading and somewhat upright plant; good vigorous habit, well branched, with early and continuous flowering response.

*Plant height.*—17-22 cm.

*Plant height (inflorescence included).*—17-22 cm.

*Plant width.*—50-60 cm.

*Garden performance and tolerance to weather.*—Very good.

*Crop time to flowering.*—About 8 weeks.

Roots:

*Number of days to initiate and develop roots.*—18-23 days at about 22 degrees C.

*Type.*—Fine, fibrous, free branching.

*Color.*—RHS N155B but whiter.

Foliage:

*Arrangement.*—Alternate, upper leaves sub-opposite.

*Immature, leaf color, upper surface.*—RHS 146B.

*Lower surface.*—RHS 146C.

*Mature, leaf color, upper surface.*—Closest to RHS 146A but more green.

*Lower surface.*—RHS 146B.

*Length.*—3.3-4.0 cm.

*Width.*—1.6-1.9 cm.

*Shape.*—Elliptical.

*Base shape.*—Attenuate.

*Apex shape.*—Obtuse to slightly acute.

*Margin.*—Entire.

*Texture, upper surface.*—Hirsute, glandular hairs.

*Lower surface.*—Hirsute, glandular hairs.

*Color of veins, upper surface.*—RHS 144A to RHS 144B.

*Color of veins, lower surface.*—RHS 144A to RHS 144B.

*Petiole color.*—RHS 144A to RHS 144B.

*Length.*—0.9-1.0 cm.

*Diameter.*—0.25-0.30 cm.

*Texture.*—Hirsute, glandular hairs.

Stem:

*Color of stem.*—RHS 146B.

*Length of stem.*—About 35 cm.

*Diameter.*—0.3 cm.

*Length of internodes.*—0.5-1.0 cm.

*Texture.*—Pilose, glandular hairs.

*Color of peduncle.*—RHS 146B.

*Length of peduncle.*—3.7-4.0 cm.

*Peduncle diameter.*—0.15 cm.

*Texture.*—Pilose, glandular hairs.

Inflorescence:

*Type.*—Flowers appear solitary in upper leaf axis.

*Floret type.*—Funnel-shaped; 5 lobed petals; fused at the base; calyx, 5 deeply lobed sepals.

*Blooming habit.*—Continuous throughout the growing season. Good floriferousness.

*Quantity of inflorescences per plant.*—Approximately 75 open flowers with 20 buds.

*Lastingness of individual blooms on the plant.*—About 4-8 days.

*Fragrance.*—Slightly sweet.

Bud (just when opening/showing color):

*Color.*—About RHS 150D with more green, with a diffused hue of RHS N81A at the apex on the inside of the lobes.

*Length.*—2.0-2.3 cm.

*Width.*—0.4-0.5 cm.

*Shape.*—Oblong.

Immature inflorescence:

*Diameter.*—2.5 cm.

*Color, upper surface.*—RHS N80A.

*Lower surface.*—RHS N81D but lighter.

Mature inflorescence:

*Floret horizontal diameter.*—3.0-3.2 cm.

*Vertical depth.*—3.0-3.3 cm.

*Petal color, upper surface.*—Closest to RHS N78B fading to about RHS 94B to RHS 94C with mostly indistinct mid-veins but sometimes showing as RHS N155B.

*Lower surface.*—RHS N81D but lighter.

*Petal apex shape.*—Slightly retuse.

*Petal base shape.*—Fused.

*Petal margin.*—Entire.

*Waviness of petals.*—Moderate.

*Petal lobation.*—Moderate.

*Petal texture.*—Papillose.

*Corolla tube color inside.*—RHS 155D but whiter.

*Outside.*—RHS 155D but whiter with RHS 144C veins.

*Corolla tube length.*—2.1-2.3 cm.

*Corolla Texture, inside.*—Papillose.

*Outside.*—Pilose, glandular hairs.

Calyx:

*Color, upper surface.*—RHS 144A.

*Lower surface.*—RHS 144A but a little darker.

*Length.*—0.9-1.2 cm.

*Width.*—0.2-0.35 cm.

*Shape.*—Almost linear.

*Apex shape.*—Obtuse.

*Based.*—Fused.

*Margins.*—Entire.

*Texture, upper surface.*—Pilose, glandular hairs.

*Lower surface.*—Pilose, glandular hairs.

Reproductive organs:

*Pistil.*—1.

*Length.*—1.7 cm.

*Style color.*—RHS 144B with RHS 144A at the tip.

*Style length.*—1.3 cm.

*Stigma color.*—RHS 144B with RHS 144A patches.

*Ovary color.*—RHS 146B.

*Stamens:* 5.

*Color of filaments.*—RHS N155D.

*Length filaments.*—1.5 cm.

*Anther color.*—RHS 160D.

*Anther length.*—0.2 cm.

*Anther shape.*—Reniform.

*Color of pollen.*—RHS 160B but lighter.

*Pollen amount.*—Moderate.

*Fertility/seed set.*—Has not been observed on this hybrid.

Disease/pest resistance: Disease/pest resistance has not been observed on this hybrid.

What is claimed is:

1. A new and distinct variety of *Petunia* plant named 'Pic Amthe' substantially as illustrated and described herein.

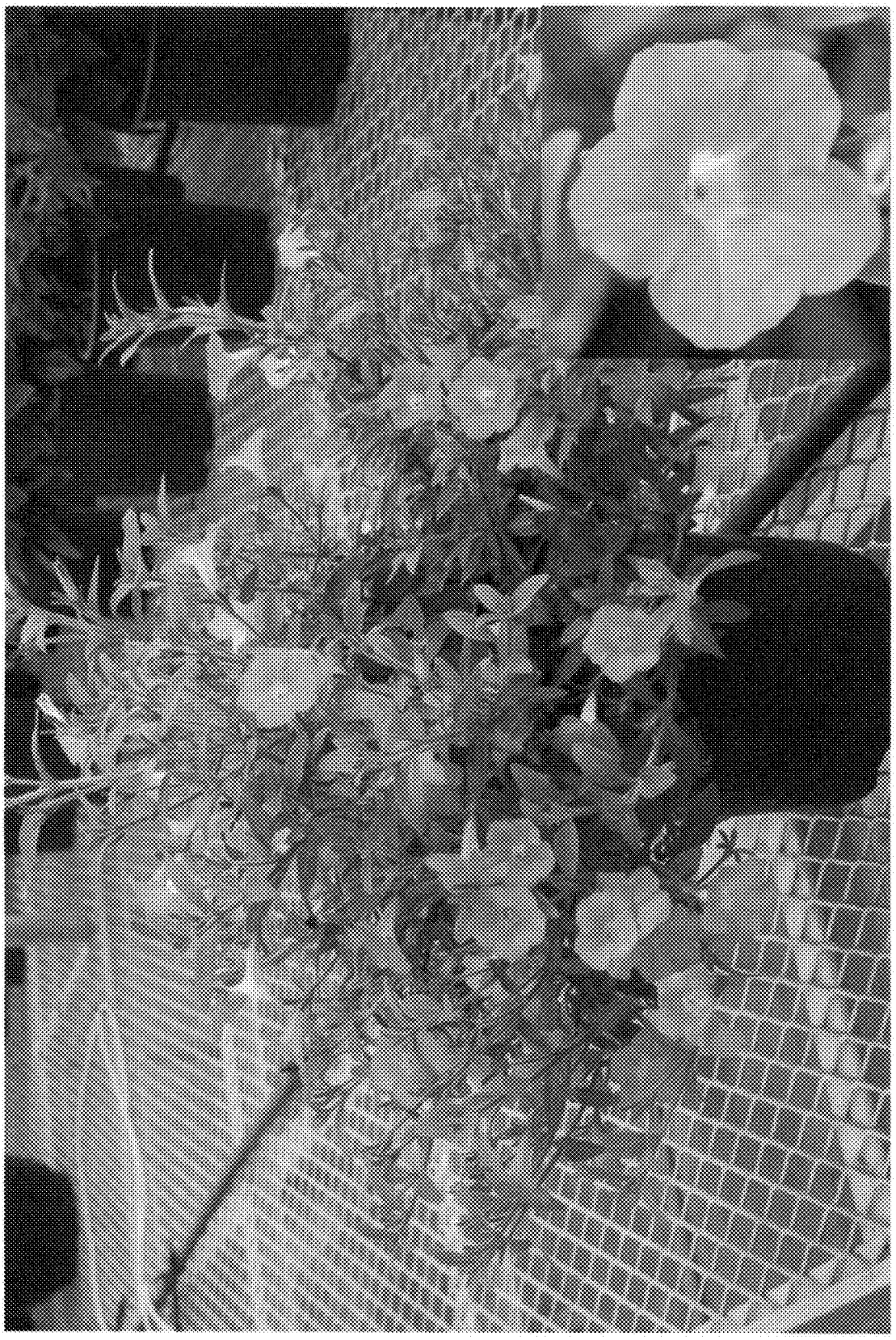

* * * * *